United States Patent [19]

Cannon, III et al.

[11] 4,168,711
[45] Sep. 25, 1979

[54] REVERSAL PROTECTION FOR RLC DEFIBRILLATOR

[75] Inventors: Robert L. Cannon, III, Waltham; Robert A. McEachern, Wellesley, both of Mass.

[73] Assignee: American Optical Corporation, Southbridge, Mass.

[21] Appl. No.: 913,705

[22] Filed: Jun. 8, 1978

[51] Int. Cl.² .............................................. A61N 1/36
[52] U.S. Cl. .............................................. 128/419 D
[58] Field of Search .................................... 128/419 D

[56] References Cited
U.S. PATENT DOCUMENTS

| 3,258,013 | 6/1966 | Druz | 128/419 D |
|---|---|---|---|
| 3,527,229 | 9/1970 | Kempen | 128/419 D |
| 4,038,990 | 8/1977 | Thompson | 128/419 PG |

Primary Examiner—William E. Kamm

Attorney, Agent, or Firm—Jeremiah J. Duggan; Alan H. Spencer; Stephen A. Schneeberger

[57] ABSTRACT

A defibrillator, or alternatively, paddles therefor adapted with the wave-forming inductance of the discharge circuit disposed between the two paddles of the discharge circuit of the defibrillator and is so disposed in the paddles as to couple in a cancelling manner when the paddles are placed face-to-face. In a preferred embodiment, the waveform inductance is split substantially equally in each of the two paddles wherein each of the inductors have a value of substantially half the total necessary inductance for the forming of the waveform for the defibrillating wave.

The respective coils of the inductors are wound in reverse directions, one with respect to the other so that the total inductance generated in a discharge directly through the paddles is substantially nil.

3 Claims, 3 Drawing Figures

320 WATT-SEC DISCHARGE INTO 50Ω LOAD

REVERSAL PROTECTION FOR RLC DEFIBRILLATOR

BACKGROUND OF THE INVENTION

This invention relates to apparatus for delivering an electrical shock in the treatment of cardiac disorders. Cardiac arrythmias may be treated by the use of various drugs such as quinidine, procainamide, digitalis and the like. Additionally, electrical depolarizing impulses of varying voltage and current are utilized in reverting arrythmias.

Apparatus for delivering these electrical depolarizing impulses falls generally into two categories being AC defibrillators and DC defibrillators. During the period since the early 1960's, utilization of DC defibrillators has gained over the utilization of AC defibrillators for a variety of medical reasons. Several of these are reported in the article from the *American Journal of Cardiology* August 1962, Volume X, No. 2, pages 223-233 entitled "Comparison of Alternating Current with Direct Current Electroshock Across the Closed Chest", Bernard Lown et al.

The DC defibrillator utilizing electroshock is presently available from a variety of sources and can include in addition to the basic circuitry for generating, storing and delivering the shock many additional features. Among these additional features may be apparatus for monitoring the EKG wave of the patient to whom the electroshock is to be delivered. Additionally, it has been determined that since the effect of the electrical shock in restoring or stabilizing heart action is dependent upon the portion of the cardiac cycle in which the shock is delivered, synchronizing apparatus is often included to avoid the shock being delivered during that portion of a cardiac cycle in which adverse effects of the shock are anticipated. Apparatus having this capability is sold in one form under the trademark "Cardioverter" and is available from American Optical Corporation, Medical Division, Bedford, Massachusetts.

In addition to determining that the effect of the electrical discharge upon restoration of the cardiac cycle is dependent upon the time of the cycle in which the shock is delivered, it has also been determined that the waveform of the discharge has a substantial impact upon the beneficial effect of the electrical shock. In DC defibrillators, the electrical charge for delivery to the patient is stored in a capacitor which is charged either from an AC source or a DC source such as a battery. Since the customary waveform of a discharge from the capacitor is not optimum for cardiac resuscitation or synchronized defibrillation, wave shaping elements are included in the discharge circuit so that the appropriate wave shape may be delivered to the resuscitating paddles which are applied to the patient's chest area. Conventional DC defibrillators often include a charged storing capacitor of a size of approximately 16 microfarads and include serially in the discharge circuit an inductor having a value of approximately 100 millihenries. In the synchronized defibrillators available from American Optical Corporation, the waveform provided is that developed by Dr. Bernard Lown. It is characterized by the rise time of more than 500 microseconds to a peak value of less than 3000 volts. The duration of the waveform is approximately 5 milliseconds and is further characterized by a momentary undershoot of the opposite polarity on the trailing edge of the waveform. It is felt by Dr. Lown that this general form aids in the restoration of the heart's electrolyte balance. Conventional defibrillators either synchronized or otherwise deliver either similar waveforms or those suggested by others such as Edmark which appreciably vary from the overall characteristics above described.

The use of DC defibrillators has seen wide acceptance in recent years in portable apparatus which is carried by emergency rescue teams since the electrical shock delivered by the DC defibrillator can be provided to the charging capacitor by battery. The instrument is fully portable and may thus be carried in trucks, ambulances or the like where the instrument may be plugged into vehicular power (6 to 12 volt DC) or may be operated from the self-contained battery.

Attendant with the wide acceptance of portable units by emergency medical service units, increased emphasis has been placed on manufacturers to produce lightweight, extremely-compact units. Accordingly, a portion of this compactness has been achieved from the use of newly developed capacitor storage devices which include new dielectric materials permitting closer placement of the capacitor plates.

Additionally, with the wide application of this instrumentation in field units, the practice has developed of testing the functionality of the unit by shorting the paddles together and discharging the unit therethrough.

We have determined that while this practice has continued for several years now, prior to our discovery of its impact on the deterioration of life of DC defibrillators this accelerated deterioration in general was not resolved. We have determined that during the course of discharge through the shorted paddles, a voltage ringing occurs. This voltage ringing manifests itself in current reversals through the discharge circuit including the wave-shaping inductor and apparently has a substantial adverse effect on the charge storage capacitor. The voltage reversals currently reach high potential, e.g., approximately double that normally stored on the capacitor. We have determined that this repeated voltage reversal manifests itself in the breakdown of the dielectric material in the capacitor, rendering the defibrillator inoperative.

The present invention overcomes the problems discovered which are inherent in the discharge of the DC defibrillator directly through the paddles. The improvement is accomplished without material impact upon the performance of the synchronized defibrillator during the therapeutic function, namely, the amount and waveform of the electrical shock is not affected by the solution to the problem as perceived by us.

REFERENCES TO THE PRIOR ART

Reference to the prior art in addition to the aforementioned article the following references may be of interest as disclosing apparatus related to the present invention. None of the cited references, however, are believed to anticipate the present invention as none are directed to the problems observed by us. Likewise, none appear to exhibit any of the features of the present invention which suggest solutions to the problems of which we became aware. These references are offered as being illustrative of the art of which we are aware and are not suggested as exhaustive of the relevant art.

U.S. Pat. No. 3,224,447 to Becker et al, Dec. 21, 1965 and U.S. Pat. No. 3,467,863 to Harsh dated Sept. 16, 1969 relate to electrodes or paddles for defibrillators.

U.S. Pat. No. 3,236,239 to Berkovits dated Feb. 22, 1966 and assigned to the Assignee of the present invention as well as U.S. Pat. No. 3,224,447 above referred to, disclose DC defibrillators and internal circuits therefor. Both of these apparatus show the capacity storage devices as well as the inductive element for wave shaping.

Numerous other examples of defibrillators and related equipment may exist in U.S. Class/28, Subclasses 419, 420, 421 and 422, however, we are aware of none which directly relate to the problem solved by the present invention or apparatus therefor.

SUMMARY OF THE INVENTION

Certain features of the present invention are disclosed in conjunction with apparatus for delivering electrical shock in the treatment of certain cardiac disorders. The particular apparatus in which the present invention may be found includes DC defibrillator having a charging capacitor and a dual branch discharge circuit a branch of which is coupled to either side of the capacitor and the other branch is coupled to the other side of the capacitor. In operation, the two branches are contacted through electrode means commonly known as defibrillator paddles to the chest of an individual to whom the electrical shock is to be applied. Such defibrillators conventionally include a wave-shaping circuit in the form of an inductor disposed in the one branch of said discharge circuit.

In accordance with one of the features of the present invention, the wave-forming inductance is divided according to a predetermined ratio and is disposed in each of the respective paddles of the discharge circuit which are connected to the charge storage capacitor. The inductance is disposed in the respective legs of the discharge circuit with the respective inductive windings electrically opposing each other when the paddles are shorted together.

Additional features of the invention will be apparent from the specification and the drawings attached thereto.

DESCRIPTION OF THE PREFERRED EMBODIMENTS

Figure 1:
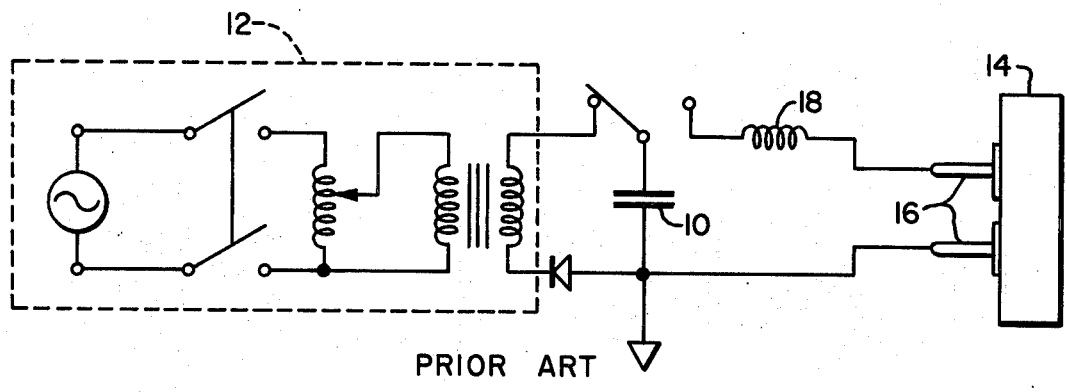
FIG. 1 is a schematic illustration of a defibrillator according to the prior art.

Referring now to the drawings and FIG. 1 in particular, the scope and application of the present invention may be understood. FIG. 1 is a simplified schematic diagram of a defibrillator as exists in the prior art. Reference 10 indicates a capacitor which is charged through a charging source 12 to ultimately be discharged to a load 14 which in the usual circumstance is a patient requiring defibrillation. Discharge is normally effected through paddles 16 which are applied to the chest cavity of the patient in a well-known medical practice. In order to ensure that the charge applied to the chest cavity is of a suitable waveform to effect depolarization of the heart, inductor 18 is added in the circuit. The combination of capacitance 10 and inductance 18 and the inherent resistance of the circuit are adjusted such that the desired waveform is achieved. Selection of these parameters for these elements is well within the skill of the art and has been described in such publications as Lown, et al, *American Journal of Cardiology*, Volume 10, No. 2, pp 223-233, 1962 "Comparison of Alternating Current with Direct Current Electroshock Across the Closed Chest".

Figure 2:
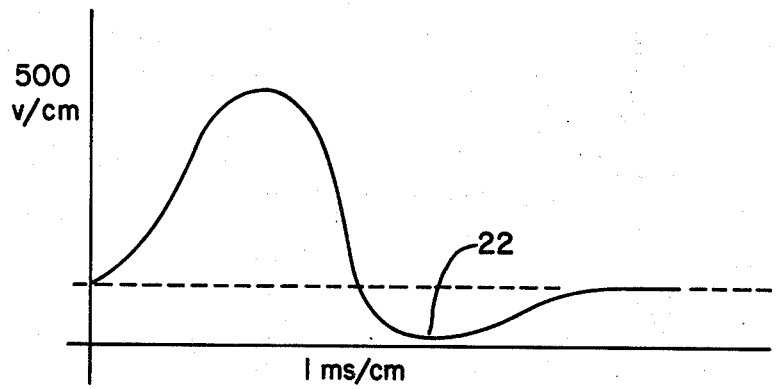
FIG. 2 is a graphic illustration of a preferred waveform for use in defibrillators.

One of the widely accepted wave forms as being appropriate for defibrillation or depolarization of the heart is known as the Lown Waveform. This waveform 20 is illustrated in FIG. 2. As this waveform is illustrated, it is characterized by rise time of more than 500 microseconds to a peak value of less than 3000 volts. Its duration is characteristically less than 5 milliseconds and normally such as 4.3 milliseconds. It should be noted that the Lown waveform is further characterized by a momentary undershoot of the opposite polarity as indicated at 22. Dr. Bernard Lown has determined that the momentary undershoot of the waveform to opposite polarity aids in the restoration of the heart's electrolytic balance.

In conventional DC capacitor charge defibrillators, the capacitor 10 may take a value of 16 microfarads and the inductance 18 100 millihenries. In such circuits, in order to produce the waveform described in FIG. 2, the inherent resistance of the full discharge circuit is approximately 50 ohms.

As indicated earlier in the specification, due to the large charge accumulated on a capacitor for relatively instantaneous discharge, there is a substantial adverse impact on the discharge circuit should the capacitor be discharged through the inductor and through the paddles shorted together. Such a discharge is essentially "no load" and substantial transient voltages and currents are developed which have adverse effect on some of the circuit components. It is apparent that such practice has become common to the users of DC defibrillators in the testing of the units to assure proper performance. It has been theorized that due to the instantaneous discarge through only a nominal resistance in a circuit such as when the paddles 16 are shorted together, that a voltage reversal occurs within capacitor 10. It is further theorized that this voltage reversal might be explained by the mechanism of electrical charge being accumulated within the dielectric material, as well as across the capacitor plates such that when the charge on the capacitor is effectively reversed during the shorted discharge test, the actual capacitor and dielectric may see an effective voltage therebetween of approximately twice that stored on the capacitor. It is further theorized that this instantaneous extremely high voltage exceeds the working capabilities of the capacitor and is material to the breakdown thereof.

We have determined that the inductor 18 acts in conjunction with capacitor 10 and the dielectric thereof in establishing this abnormally high voltage reversal observed during shorting of the paddles. Effectively, in the "no load" discharge configuration, the capacitor and inductor form an oscillator through which several transient voltage reversals may occur. We have further determined that during such a short situation, if the inductance 18 were allowed to cancel itself, that capacitor 10 sees only a nominally increased voltage during a short test discharge, thereby avoiding the destructive "ringing".

Figure 3:
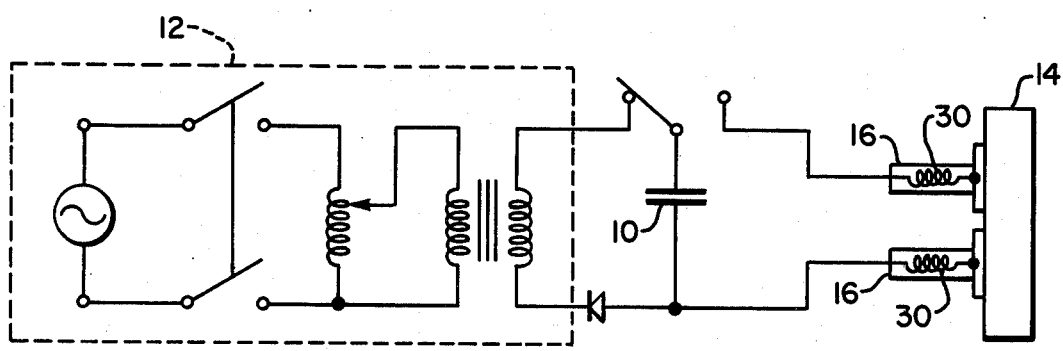
FIG. 3 is a schematic illustration of a preferred form of the present invention.

Referring now to FIG. 3 of the drawings, it may be observed how the described problem can be overcome by the inclusion of self-cancelling inductance in the discharge circuit, in the event of a short test through the paddles. We have determined that by the inclusion of a portion of the wave-shaping inductance 30 in each of the paddles 16 having a total value still in the order of that conventionally used, however split, say 50—50, it overcomes the observed voltage reversal and deterioration of capacitor 10. Inductance 30 in each of the two paddles 16 is wound such that when the paddles are placed together the inductance is cancelling, namely the coils 30 are wound in loops having the direction of current, and thus the flux generated, opposing with respect to each other when connected together.

It is necessary that the coils be so housed in the paddles 16 such that the fields are not shielded, or otherwise prevented from inductive coupling. Further, the spacing of the inductors when the paddles are shorted must be such that more than one half of the total inductive of the circuit is cancelled. Accordingly, it should be recognized that, the greater the degree of coupling, the less equally the inductance needs to be split between the paddles. This flexibility may be of substantial importance in those portable defibrillators wherein one of the paddles forms a part of the case of the unit and the other paddle is detachable for therapeutic use. Design criteria may dictate placing as much inductive as practical within the defibrillators case to promote compactness of the separate paddle.

The invention may be embodied in other specific forms without departing from the spirit or central characteristics thereof. The present embodiments are therefore to be considered in all respects as illustrative and not restrictive in the scope of the invention as indicated by the pending claims rather than by the foregoing description. All changes which come within the meaning and range of equivalency of the claims are therefore intended to be embraced therein.

We claim:
1. In apparatus for cardiac therapy including defibrillator means having a capacitor, a charging source for said capacitor, a discharge circuit for said capacitor including a pair of electrodes adapted to apply the discharge of said capacitor to a patient, a wave-shaping inductor disposed in said discharge circuit, switch means for selectively connecting said capacitor to said charging means or said discharge circuit;

the improvement comprising the inclusion of at least a portion of said inductive discharge wave-shaping means disposed in one of said patient electrodes, and at least a portion of said inductive discharge wave-shaping means disposed in the other of said patient electrodes, said inductances being disposed such that their individual inductive coils are oppositely wound and flux fields opposing when shorted together.

2. In a patient electrode for connection to a defibrillator having a capacitor, a charging source for said capacitor, a discharge circuit for said capacitor including a wave-shaping inductor, switch means for selectively connecting said capacitor to said charging means or said patient electrode, the improvement comprising wave-shaping inductance disposed in said patient electrode, said inductance being wound in a predetermined first direction and being adapted to inductively couple with wave-shaping inductance disposed in a second patient electrode having inductance being wound in a predetermined second direction so that when said electrode is shorted to said second electrode the inductive fluxes oppose and tend to cancel the wave shaping inductance.

3. The improvement according to claim 2 wherein said first inductance and said second inductance are in a ratio of from 1:1 to 1.15: 0.85.

* * * * *